US008868181B2

(12) United States Patent
Lang et al.

(10) Patent No.: US 8,868,181 B2
(45) Date of Patent: Oct. 21, 2014

(54) IMPLANTABLE ELECTROSTIMULATOR

(75) Inventors: Volker Lang, West Linn, OR (US); Jie Lian, Beaverton, OR (US); Dirk Müssig, West Linn, OR (US)

(73) Assignee: Biotronik CRM Patent AG (CH)

(*) Notice: Subject to any disclaimer, the term of this patent is extended or adjusted under 35 U.S.C. 154(b) by 1764 days.

(21) Appl. No.: 11/383,232

(22) Filed: May 15, 2006

(65) Prior Publication Data
US 2007/0265670 A1 Nov. 15, 2007

(51) Int. Cl.
*A61N 1/362* (2006.01)
*A61N 1/368* (2006.01)

(52) U.S. Cl.
CPC .......... *A61N 1/3622* (2013.01); *A61N 1/3682* (2013.01)
USPC .......................................................... 607/9

(58) Field of Classification Search
USPC ............... 607/2, 4, 9, 11, 14, 15, 27; 600/518
See application file for complete search history.

(56) References Cited

U.S. PATENT DOCUMENTS

| | | | |
|---|---|---|---|
| 4,284,082 A * | 8/1981 | Funke et al. | 607/9 |
| 4,941,471 A | 7/1990 | Mehra | |
| 5,312,451 A | 5/1994 | Limousin et al. | |
| 5,545,185 A | 8/1996 | Denker | |
| 5,814,085 A | 9/1998 | Hill | |
| 6,078,836 A * | 6/2000 | Bouhour et al. | 607/14 |
| 6,813,518 B2 * | 11/2004 | Kupper | 607/14 |
| 2001/0034488 A1* | 10/2001 | Policker et al. | 600/515 |
| 2004/0127943 A1* | 7/2004 | Henry et al. | 607/4 |
| 2004/0147968 A1* | 7/2004 | Casset | 607/17 |
| 2005/0240235 A1* | 10/2005 | Limousin et al. | 607/9 |

FOREIGN PATENT DOCUMENTS

| | | |
|---|---|---|
| EP | 0 550 342 B1 | 6/1997 |
| WO | WO 83/01389 A | 4/1983 |
| WO | WO 02/053228 A | 7/2002 |

OTHER PUBLICATIONS

Denker et al., 1984, Facilitation of Ventricular Tachycardia Induction with Abrupt Changes in Ventricular Cycle Length, *The American Journal o Cardiology*, vol. 53, pp. 508-515.
El-Sherif & Turitto, 1999, The Long QT Syndrome and Torsade De Pointes. *PACE*, vol. 22, pp. 91-110.
Fromer and Wietholt, 1999, Algorithm for the Prevention of Ventricular Tachycardia Onset: The Prevent Study, *The American Journal of Cardiology*, vol. 83, pp. 45D-47D.

(Continued)

*Primary Examiner* — Kennedy Schaetzle
*Assistant Examiner* — Erica Lee
(74) *Attorney, Agent, or Firm* — Craig A. Fieschko, Esq.; DeWitt Ross & Stevens S.C.

(57) ABSTRACT

An implantable cardiac electrostimulator includes an atrial sensing channel generating an atrial sense event signal upon detection of atrial activity, a ventricular sensing channel generating a ventricular sense event signal upon detection of ventricular activity, a VES detector detecting ventricular extrasystoles, atrial and ventricular stimulation pulse generators, and a stimulation control unit. The stimulation control unit determines scheduled delivery times of atrial stimulation pulses (T(A)) and/or ventricular stimulation pulses (T(V)), and triggers delivery if no atrial sense event signal arises before the end of an atrial escape interval (VAI) timing out at T(A), or if no ventricular sense event signal arises before the end of a ventricular escape interval (VEI) timing out at T(V). T(A) and T(V) depend upon detection of a ventricular extrasystole, and proper atrioventricular synchrony is maintained by setting a physiologically adequate A-V-delay between T(A) and T(V).

29 Claims, 6 Drawing Sheets

(56) References Cited

OTHER PUBLICATIONS

Glikson et al., 2002, Impaired Detection of Ventricular Tachyarrhythmias by a Rate-Smoothing Algorithm in Dual-Chamber Implantable Defibrillators: Intradevice Interactions, *Journal of Cardiovascular Electrophysiology*, vol. 13, pp. 312-318.

Gomes et al., 1989, The Role of Silent Ischemia, the Arrhythmic Substrate and the Short-Long Sequence in the Genesis of Sudden Cardiac Death, *JACC*, vol. 14, No. 7, pp. 1618-1625.

Gronefeld et al., Ventricular Rate Stabilization for the Prevention of Pause Dependent Ventricular Tachyarrhythmias: Results from a Prospective Study in 309 ICD Recipients, PACE, vol. 24, No. 12, pp. 1708-1714.

Meyerfeldt et al, 1997, The mode of onset of ventricular tachycardia, *European Heart Journal*, vol. 18, pp. 1956-1965.

Roelke et al., 1994, Analysis of the Initiation of Spontaneous Monomorphic Ventricular Tachycardia by Stored Intracardiac Electrograms, *JACC*, vol. 23, No. 1, pp. 117-122.

Shivkumar et al., 2000, Intradevice Interaction in a Dual Chamber Implantable Cardioverter Defibrillator Preventing Ventricular Tachyarrhythmia Detection, *Journal of Cardiovascular Electrophysiology*, vol. 11, No. 11, pp. 1285-1288.

Strohmer et al., 2004, Delayed Detection of Stable Ventricular Tachycardia in a Dual-Chamber Implantable Cardioverter Defibrillator: What is the Mechanism?, *Pacemaker/ICD Tracing of the Month*, pp. 244-246.

Viskin et al., 1998, Prevention of Torsade de pointes in the congenital long QT syndrome: use of a pause prevention pacing algorithm, *Heart*, 79:417-419.

Viskin et al., 2000, Rate Smoothing with Cardiac Pacing for Preventing Torsade de Pointes, *The American Journal of Cardiology*, vol. 86 (9A), pp. 111K-115K.

Viskin et al, 2001, Letter to the Editor, *Journal of Cardiovascular Electrophysiology*, vol. 12, No. 5, pp. 619-621.

Search Report of the European Patent Office for EP patent application serial No. 07 007 666.6, dated Jul. 5, 2007.

\* cited by examiner

IMPLANTABLE ELECTROSTIMULATOR

FIELD OF INVENTION

The present invention relates to implantable electrostimulators, including pacemakers, defibrillators and cardioverters, which stimulate cardiac tissue electrically to control the patient's heart rhythm. In particular the present application is directed to an implantable electrostimulator comprising rate smoothing means for smoothing a heart rate or a stimulation rate, respectively, after a ventricular extra systole.

BACKGROUND OF THE INVENTION

A ventricular extra systole is an ectopic spontaneous ventricular contraction arising in the ventricles and stimulating the myocardium prematurely.

A ventricular extrasystole (VES) with a short coupling interval is frequently followed by a relatively long compensatory pause before returning to presystolic intrinsic ventricular cycle length. Such a so-called short-long sequence has adverse effects on cardiac hemodynamics due to irregular ventricular filling. Moreover, the pause-dependent ventricular instability leads to enhanced dispersion of ventricular refractoriness and thus to a higher vulnerability predisposing to sustained ventricular arrhythmias (Cranefield & Aronson, 1988). Growing evidence has indicated that both monomorphic and polymorphic ventricular tachyarrhythmias can be triggered by the short-long cycles (Denker et al., 1984; Gomes et al., 1989; Roelke et al., 1994; Meyerfeldt et al., 1997, El-Sherif & Turitto, 1999). Meanwhile, preliminary data suggest that suppression of postextrasystolic pauses by overdrive pacing can prevent the onset of ventricular tachyarrhythmias (Viskin et al., 1998, 2000).

Various methods have been proposed for ventricular rate smoothing upon detection of VES. U.S. Pat. No. 4,941,471 issued to Mehra discloses pacemakers designed to stabilize ventricular rate by continuously modulating ventricular escape interval (VEI), which is calculated to be equal to the immediate preceding VEI plus an increment. U.S. Pat. No. 5,545,185 issued to Denker discloses cardiac pacers designed to detect abrupt cycle length shortening, followed by ventricular pacing to prevent the compensatory pause. U.S. Pat. No. 5,814,085 issued to Hill discloses pacemakers designed to improve the patents of Mehra and Denker, in that the VEI is calculated as a function of the underlying heart rate, and optionally as a function of the relative prematurity of the sensed ventricular depolarization. In all the patents cited above, the rate stabilization pacing is applied to right ventricle, without consideration on AV synchronization. U.S. Pat. No. 5,312,451 issued to Limousin et al. discloses an algorithm for the control of both atrial pacing and ventricular pacing after detection of VES. Although this algorithm provides a means to stimulate atrium and ventricle synchronously, the variation of the pacing timer control parameters after VES is not physiological, and the algorithm cannot properly respond to the doublets, triplets, or repeated appearance of VES. U.S. Pat. No. 5,938,687 issued to Bouhour et al. discloses a process that intended to improve the patent of Limousin et al., by incorporating the detection and rhythm control of atrial extrasystole. However, the limitations of the pacing control after VES remain the same.

Although the feature of ventricular rate smoothing has been incorporated in some of the latest dual-chamber cardiac implantable devices to prevent postextrasystolic pause (Viskin et al., 1998; Fromer and Wietholt, 1999; Gronefeld et al., 2002), the existing rate control algorithms are mainly based on ventricular cycle length. As a result, physiologically undesirable pacing effects are likely to occur, for example, retrograde conduction by ventricular pacing without atrial capture (Viskin et al., 1998), and possible very short atrial interval due to competitive atrial pacing. Furthermore, there is clinical evidence that with certain parameter settings (long AV delay, aggressive ventricular rate smoothing, high upper tracking rate), existing ventricular rate smoothing algorithms may result in intradevice interactions that cause device failure or delay detection of sustained monomorphic ventricular tachycardia due to ventricular undersensing (Shivkumar et al., 2000; Glikson et al., 2002; Strohmer et al., 2004).

SUMMARY OF THE INVENTION

For the above reasons, there is a need for an electrostimulator providing improved heart rate smoothing after VES.

According to the invention, this need is met by an electrostimulator providing for both atrial rate smoothing and ventricular rate smoothing to suppress the compensatory pause after ventricular extrasystole. In a preferred embodiment such heart rate smoothing algorithm can minimize the risk of ventricular undersensing to prevent potential interference with ventricular tachycardia detection.

The implantable cardiac electrostimulator according to the invention comprises an atrial sensing channel for processing intracardiac electrogram signals and for detecting signals corresponding to atrial activity and for generating an atrial sense event signal upon detection of a signal corresponding to atrial activity, a ventricular sensing channel for processing intracardiac electrogram signals and for detecting signals corresponding to ventricular activity and for generating a ventricular sense event signal upon detection of a signal corresponding to ventricular activity, a VES detector being operatively connected to said atrial and ventricular sensing channel and being adapted to detect ventricular extrasystoles an atrial stimulation pulse generator a ventricular stimulation pulse generator and a stimulation control unit being operatively connected to said atrial stimulation pulse generator and said ventricular stimulation pulse generator.

The stimulation control unit is adapted to determine a scheduled time of delivery of an atrial stimulation pulse (T(A)) and a scheduled time of delivery of a ventricular stimulation pulse (T(V)). The stimulation control unit is further adapted to trigger said atrial stimulation pulse generator or said ventricular stimulation pulse generator at the scheduled point of time T(A) or T(V), respectively, if no atrial sense signal is generated before time out of an atrial escape interval (VAI), said atrial escape interval timing out at T(A), or if no ventricular sense signal is generated before time out of a ventricular escape interval (VEI), said ventricular escape interval timing out at T(V), respectively. In order to achieve the desired, inventive effect, the stimulation control unit is adapted to determine T(A) and T(V) depending upon detection of a ventricular extra systole while maintaining a proper atrioventricular synchrony by setting a physiologically adequate A-V-delay between T(A) and a corresponding T(V). Thus truly AV synchronized stimulation during rate smoothing is achieved.

Atrial activity is detected on the basis of an intracardiac electrogram (IEGM) signal corresponding to depolarization of the atrial myocardium. Similarly, ventricular activity is detected on the basis of an IEGM signal corresponding to depolarization of the ventricular myocardium.

An atrial escape interval as understood herein may be any interval between a preceding atrial or ventricular event—whether stimulated or sensed—and the point of time T(A) of the next scheduled atrial stimulation pulse. In the same manner a ventricular escape interval in the sense of this disclosure shall mean any interval between a preceding atrial or ventricular event—whether stimulated or sensed—and the point of time T(V) of the next scheduled ventricular stimulation pulse.

In the preferred embodiment of the invention as disclosed in the detailed description of the invention the ventricular escape interval is timed from a preceding ventricular event and denoted VEI (VEI: ventricular escape interval), whereas the atrial escape interval is also timed from a preceding ventricular event but is denoted VAI (VAI: V-A-interval). According to the preferred embodiment of the invention, T(A) is calculated by first calculating T(V) and then subtracting an physiologically adequate A-V-delay (AVD). Thus, a ventricular based timing is implemented.

In a similar manner, atrial based timing may be implemented as an alternative to the embodiment disclosed in detail.

In a preferred embodiment, the stimulation control unit is adapted to perform a synchronous heart rate smoothing algorithm, said algorithm comprising calculating a first ventricular escape interval (VEI) beginning with a ventricular extra systole and ending with a scheduled ventricular stimulation pulse T(V) said calculation being based on a time duration between the ventricular extra systole and the preceding ventricular event, said calculated ventricular escape interval being longer than said duration between the ventricular extra systole and the preceding ventricular event and being shorter than a base interval (BI) being applicable in the absence of a ventricular extra systole.

Preferably, the stimulation control unit determines an A-V-delay (AVD) on the basis of said calculated ventricular escape interval (VEI).

Based on said A-V-delay, a V-A-delay and the point of time T(A) of the next scheduled atrial stimulation pulse is determined. Thus, a dual-chamber pacing rate control method is provided that can not only regularize VEI, but also regularize VA interval (VAI) and AV delay (AVD), thus achieving physiologically reasonable heart rate smoothing.

In a preferred embodiment, the electrostimulator comprises:
  means for delivering pacing pulses to capture both atrium and ventricle immediately after VES if it is followed by a ventricular pause;
  rate smoothing means for synchronously pacing atrium and ventricle with gradually prolonged A-A-interval and V-V-interval, until these intervals correspond to a basic interval or until an intrinsic event is sensed.

Said rate smoothing means for synchronously pacing atrium and ventricle with gradually prolonged A-A-interval and V-V-interval comprise:
  VEI determination means for determining the first ventricular escape interval based on the coupling interval between a ventricular extra systole and the ventricular event immediately preceding said ventricular extra systole (VES coupling interval);
  said VEI determination means are adapted to ensure that the first ventricular escape interval after said ventricular extra systole is sufficiently long despite a possibly very short VES coupling interval;
  AVD determination means for determining a dynamic A-V-delay based on said ventricular escape interval (VEI) after VES;
  VAI determination means for determining a first V-A-interval starting with said ventricular extra systole and ending with a scheduled point of time T(A) of delivery of an atrial stimulation pulse based on said first ventricular escape interval and said A-V-delay;
  said VAI determination means being adapted to update said first V-A-interval when necessary to prevent competitive atrial pacing;
  VEI updating means for updating the first ventricular escape interval if the first V-A-interval is updated;
  means for determining the following (e.g. second) ventricular escape interval based on a previous (e.g. first) ventricular escape interval;
  means for determining the following V-A-interval based on the corresponding ventricular escape interval and A-V-delay;
  means for constraining each V-A-interval and ventricular escape interval within physiological range which is limited by predefined minimum and maximum intervals;
  means for deactivating said rate smoothing means upon detection of sensed atrial event before expiration of VAI, or sensed ventricular event before expiration of VEI.

A possible implementation of said electrostimulator is based on an electrostimulator comprising a control unit being adapted or programmed to perform a rate smoothing algorithm comprising the steps of:
(a) determining the first VEI based on the VES coupling interval;
(b) ensuring the first VEI sufficiently long despite the possible very short VES coupling interval;
(c) determining dynamic AVD based on said ventricular escape interval (VEI);
(d) determining the first VAI based on the first VEI and AVD;
(e) updating the first VAI when necessary to prevent competitive atrial pacing;
(f) updating the first VEI if the first VAI is updated;
(g) determining the following VEI based on previous VEI;
(h) determining the following VAI based on the corresponding VEI and AVD;
(i) constraining VAI and VEI within physiological range which is limited by predefined minimum and maximum intervals;
(j) exiting the algorithm upon detection of sensed atrial event before expiration of VAI, or sensed ventricular event before expiration of VEI.

Thus, a proper means of deactivation or reactivation of heart rate smoothing in response to different clinical events, such as false ventricular sensing, multiple VESs, and ventricular tachycardia, is provided.

Preferably the electrostimulator is adapted to determine the first VEI based on VES coupling interval by prolonging said VES coupling interval by a certain percentage or by a certain fixed interval or based on an underlying heart rate and/or a prematurity of the VES which can be measured by the ratio of the VES coupling interval to the pre-VES ventricular interval.

Similarly, an electrostimulator is preferred which is adapted to determine a following VEI based on a previous VEI by prolonging said previous VEI by a certain percentage or by a certain fixed interval or based on underlying heart rate.

Preferably the electrostimulator is further adapted to determine a VEI (including the first and the followings) such that said VEI is constrained within a predefined physiological range which should be programmable, preferably (but not limited to) between an upper tracking interval UTI and a base interval BI.

Said means for ensuring that the first VEI is sufficiently long are preferably adapted to ensure that the first VEI is not shorter than a predefined minimum interval, preferably (but not limited to) not shorter than the UTI, so that the subsequent ventricular event with very short cycle length can deactivate the heart rate smoothing algorithm, and prevent it from interfering with the ventricular tachycardia detection.

Determination of a next VEI by prolongation of a previous VEI is preferably constrained such that the VEI prolongation lies within predefined limits, for instance, VEI prolongation by a certain percentage of should not exceed an upper limit of increment interval, or alternatively, VEI increment by a fixed interval should not exceed an upper limit of prolongation percentage.

Said AV determination means are preferably adapted to determine said dynamic A-V-delay based on an instantaneous R-R-interval (interval between two consecutive ventricular sense events) or an instantaneous P-P-interval (interval between two consecutive atrial sense events) by using a linear equation as described in detail below, or by using other formulas, or by checking a predefined look-up table, or by simply using a predefined fixed value.

Said VAI determination means are preferably adapted to determine a V-A interval (including the first and the following intervals) based on corresponding VEI and AVD by calculating VAI by subtracting AVD from VEI.

Said VAI updating means for updating the first VAI when necessary preferably include means for evaluating the time interval between the first sensed atrial event after VES (if there is one) and the scheduled first atrial stimulation pulse, and are adapted to ensure that the V-A-interval is not shorter than a predefined minimum interval, preferably (but not limited to) the upper tracking interval UTI.

Said VEI updating means for updating the first ventricular escape interval VEI if the first V-A-interval is updated preferably are adapted to recalculate the first ventricular escape interval VEI as the sum of the updated first V-A-interval and the first A-V-delay, which can be a predefined interval, or is preferably recalculated based on updated atrial interval or ventricular interval.

By achieving these means, the present invention provides implantable cardiac devices featuring a robust heart rate smoothing algorithm to eliminate the VES-dependent compensatory pause. The present invention is directed to implantable cardiac devices that can deliver pacing pulses to both atrium and ventricle, as well as can sense events in both chambers.

The VES is detected and the heart rate smoothing algorithm is activated upon detection of a sensed ventricular event that is not coupled with a preceding atrial event (either paced or sensed). The preceding atrial event and the following ventricular event are defined as coupled if their time interval is within the predefined physiological range of AVD. The present heart rate smoothing algorithm is designed to capture both atrium and ventricle immediately after VES detection, provided that there is an associated postextrasystolic pause. Constraints are made to ensure there is no competitive atrial pacing, and both VEI and VAI are not shorter than certain minimum duration, preferably the upper tracking interval (UTI). Thereafter, the algorithm controls atrial pacing and ventricular pacing in a synchronous manner, by beat-to-beat modulation of VEI, VAI, and AVD, until the intrinsic cardiac event breaks in, or until the predefined basic interval (BI) is reached.

By this means, not only ventricular rate, but also atrial rate and AV delay are smoothly regulated after VES, thus achieving truly heart rate smoothing. Furthermore, because VAI and AVD are dynamically adjusted, in the case of monomorphic ventricular tachycardia, the risk of ventricular events falling into blanking periods (alternating between postatrial and postventricular blanking periods) will be minimized. This will eliminate or significantly ameliorate the absence detection of ventricular tachycardia (Glikson et al. 2002). In addition, the algorithm is automatically deactivated in response to sensed rapid ventricular events due to false ventricular sensing, multiple VESs, and ventricular tachycardia, while is reactivated immediately upon detection of any new VES.

The ventricular rate smoothing after VES is equally well suited for use in electrostimulators like dual chamber pacemakers, a cardioverter/defibrillators or multi chamber pacemakers for cardiac resynchronization therapy (CRT) or in a combination of these.

DETAILED DESCRIPTION OF THE DRAWINGS

Figure 1:
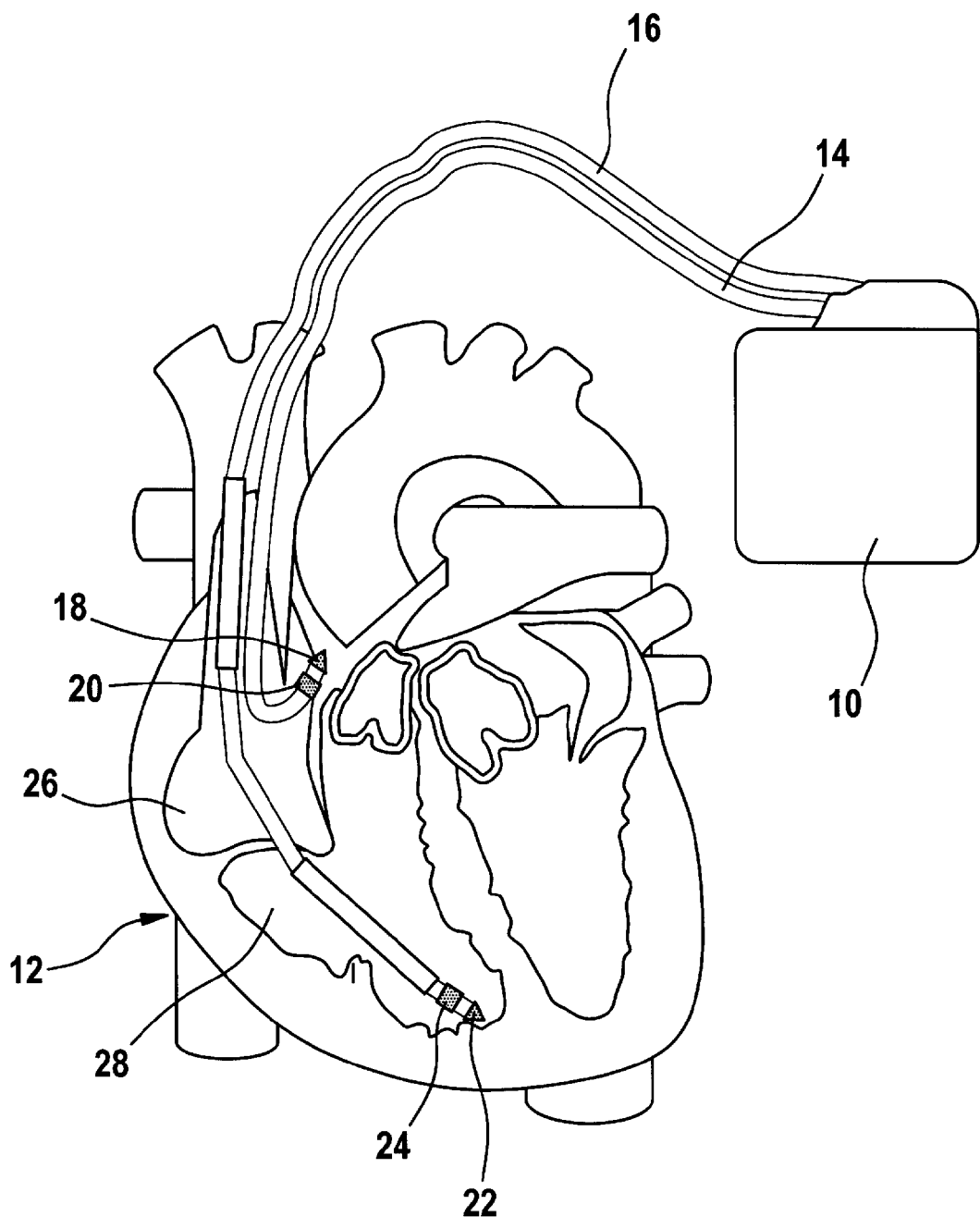
FIG. 1 shows a dual chamber pacemaker connected to pacing/sensing leads placed in a heart
Figure 2:
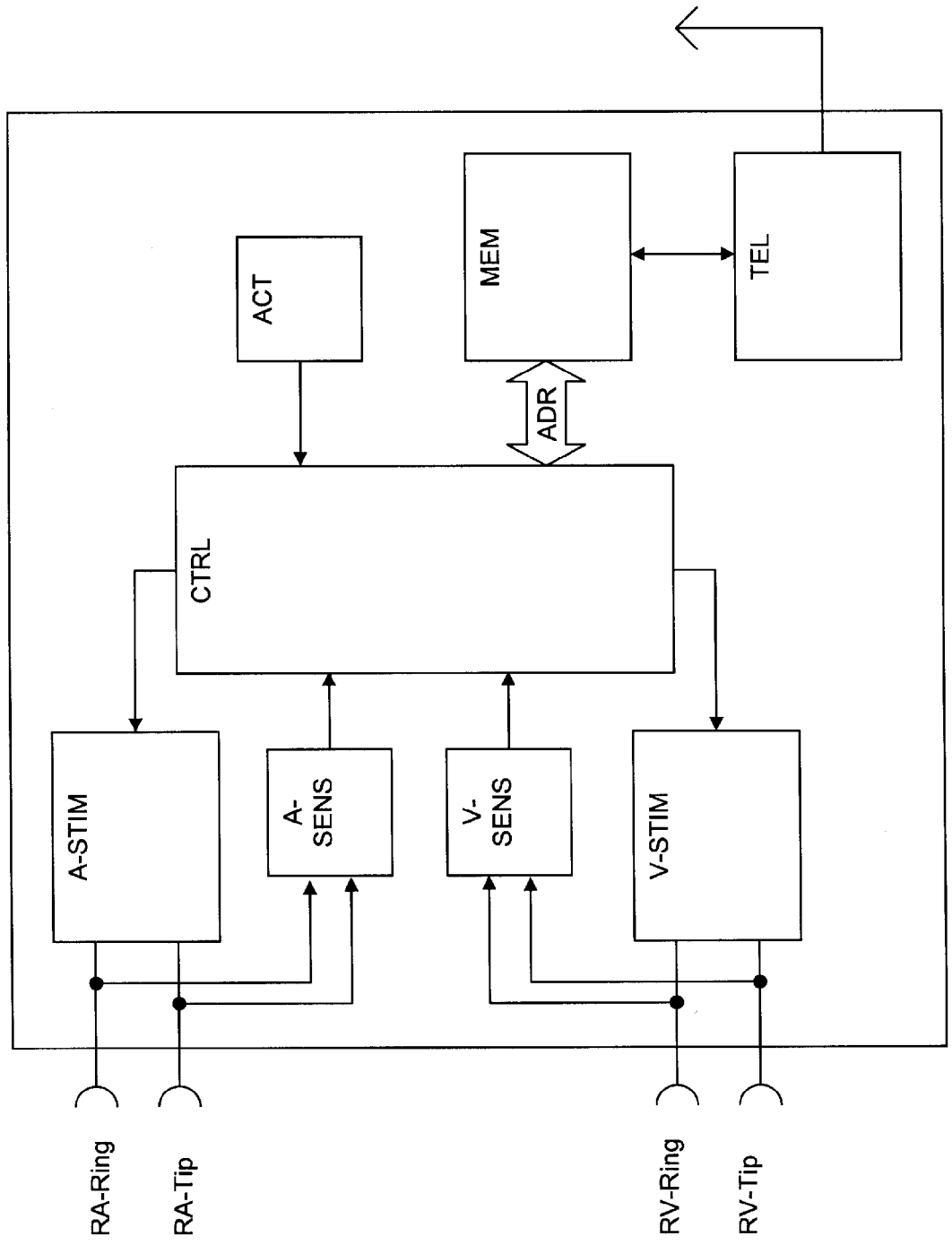
FIG. 2 shows a schematic block diagram of a pacemaker according to the invention.

In FIGS. 1 and 2 an electrostimulator according to the invention is illustrated by way of an exemplary dual chamber pacemaker 10 (pacer 10).

Referring to FIG. 1 a dual chamber pacemaker 10 connected to pacing/sensing leads placed in a heart 12 is illustrated. The pacemaker 10 is coupled to a heart 12 by way of leads 14 and 16, the lead 14 having a pair of right atrial electrodes 18 and 20 that are in contact with the right atria 26 of the heart 12, and the lead 16 having a pair of electrodes 22 and 24 that are in contact with the right ventricle 28 of heart 12. The electrodes 18 and 22 are tip-electrodes at the very distal ends of leads 14 and 16, respectively. Electrode 18 is a right atrial tip electrode RA-Tip and electrode 22 is a right ventricular tip electrode 22. Electrodes 20 and 24 are designed as ring electrodes in close proximity to but electrically isolated from the respective tip electrodes 18 and 22. Electrode 20 forms a right atrial tip electrode RA-Ring and electrode 24 forms a right ventricular ring electrode RV-Ring.

Referring to FIG. 2 a simplified block diagram of a dual chamber pacemaker 10 is illustrated. During operation leads 14 and 16 are connected to respective output/input terminals of pacemaker 10 as indicated in FIG. 1 and carry stimulating pulses to the tip electrodes 18 and 22 from an atrial stimulation pulse generator A-STIM and a ventricular pulse generator V-STIM, respectively. Further, electrical signals from the atria are carried from the electrode pair 18 and 20, through the lead 14, to the input terminal of an atrial channel sense amplifier A-SENSE; and electrical signals from the ventricles are carried from the electrode pair 22 and 24, through the lead 16, to the input terminal of a ventricular sense channel amplifier R-SENSE.

Controlling the dual chamber pacer 10 is a control unit CTRL which is connected to the sense amplifiers A-SENSE and V-SENSE and to the stimulation pulse generators A-STIM and V-STIM. Control unit CTRL receives the output signals from the atrial sense amplifier A-SENSE and from the ventricular sense amplifier V-SENSE. The output signals of sense amplifiers A-SENSE and V-SENSE are generated each time that a P-wave or an R-wave, respectively, is sensed within the heart 12.

Control unit CTRL also generates trigger signals that are sent to the atrial stimulation pulse generator A-STIM and the ventricular stimulation pulse generator V-STIM, respectively. These trigger signals are generated each time that a stimulation pulse is to be generated by the respective pulse generator A-STIM or V-STIM. The atrial trigger signal is referred to simply as the "A-pulse", and the ventricular trigger signal is referred to as the "V-pulse". During the time that either an A-pulse or V-pulse is being delivered to the heart, the corresponding sense amplifier, A-SENSE and/or R-SENSE, is typically disabled by way of a blanking signal presented to these amplifiers from the control unit CTRL, respectively. This blanking action prevents the sense amplifiers A-SENSE and V-SENSE from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Still referring to FIG. 2, the pacer 10 may also include a memory circuit MEM that is coupled to the control unit CTRL over a suitable data/address bus ADR. This memory circuit MEM allows certain control parameters, used by the control unit CTRL in controlling the operation of the pacemaker 10, to be programmably stored and modified, as required, in order to customize the pacemaker's operation to suit the needs of a particular patient. Such data includes the basic timing intervals used during operation of the pacemaker. Further, data sensed during the operation of the pacer may be stored in the memory MEM for later retrieval and analysis.

A telemetry circuit TEL is further included in the pacemaker 10. This telemetry circuit TEL is connected to the control unit CTRL by way of a suitable command/data bus. Telemetry circuit TEL allows for wireless data exchange between the pacemaker 10 and some remote programming or analyzing device which can be part of a centralized service center serving multiple pacemakers.

The pacemaker 10 in FIG. 1 is referred to as a dual chamber pacemaker because it interfaces with both the right atrium 26 and the right ventricle 28 of the heart 10. Those portions of the pacemaker 10 that interface with the right atrium, e.g., the lead 14, the P-wave sense amplifier A-SENSE, the atrial stimulation pulse generator A-STIM and corresponding portions of the control unit CTRL, are commonly referred to as the atrial channel. Similarly, those portions of the pacemaker 10 that interface with the right ventricle 28, e.g., the lead 16, the R-wave sense amplifier V-SENSE, the ventricular stimulation pulse generator V-STIM, and corresponding portions of the control unit CTRL, are commonly referred to as the ventricular channel.

In order to allow rate adaptive pacing in a DDDR mode, the pacemaker 10 further includes a physiological sensor ACT that is connected to the control unit CTRL of the pacemaker 10. While this sensor ACT is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

Now, the operative behavior of the pacemaker according to the invention shall be described. This behavior is achieved by adapting control unit CTRL to behave as described hereinafter.

Generally, control unit CTRL will trigger an atrial stimulation pulse (A-pulse) at a calculated point of time T(A) previously determined by the control unit CTRL as further illustrated bellow unless an atrial sense signal is generated by the P-wave sense amplifier A-SENSE before triggering the atrial stimulation pulse generator A-STIM at T(A).

Similarly, control unit CTRL will trigger a ventricular stimulation pulse (A-pulse) at a calculated point of time T(V) previously determined by the control unit CTRL as further illustrated bellow unless ventricular sense signal is generated by the R-wave sense amplifier V-SENSE before triggering the ventricular stimulation pulse generator V-STIM at T(V).

To determine T(V) control unit CTRL calculates a ventricular escape interval VEI. Each ventricular escape interval VEI begins with the latest ventricular event (sensed or stimulated) and ends at the point of time of the next scheduled ventricular stimulation pulse T(V). Calculation of an actual a ventricular escape interval VEI is based on the duration of the latest interval between to ventricular events, the R-R interval (RRI).

After having thus determined an actual ventricular escape interval VEI, control unit CTRL calculates an adequate A-V delay. The A-V delay is the time duration between the next atrial stimulation pulse to be scheduled and the scheduled ventricular stimulation pulse at T(V) at the end of the actual ventricular escape interval VEI. Then, the point of time of the next scheduled atrial stimulation pulse T(A) can be calculated by subtracting the actual A-V delay AVD from T(V). Thus, the next scheduled point of time for triggering an atrial stimulation pulse T(A) is determined and the end of an V-A interval spanning from the latest ventricular event (sensed or stimulated) to the actual T(A). The A-V interval AVI can be referred to as an atrial escape interval in the sense of this disclosure.

When calculating each T(V) and T(A), control unit CTRL checks that the resulting intervals, RRI (the interval between two consecutive ventricular events, sensed or stimulated) and PPI (the interval between two consecutive atrial events, sensed or stimulated) are shorter than a base interval BI (BI being the longest interval between two consecutive events).

Similarly, control unit CTRL checks that RRI and PPI are longer than an upper tracking interval UTI. The upper tracking interval UTI is the interval resulting from a predetermined maximum pacing rate (upper tracking rate).

Figure 3:
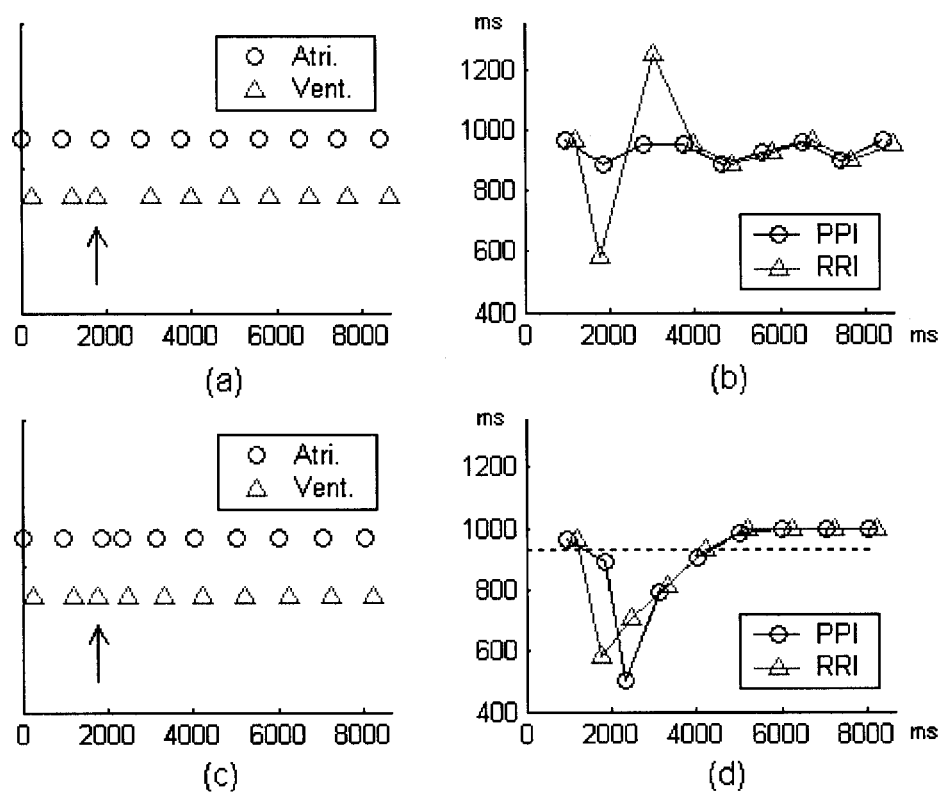
FIG. 3 shows representative plots illustrating the effect of the present heart rate smoothing algorithm upon detection of an isolated VES.

FIG. 3 shows a representative illustration of the synchronous heart rate smoothing and the resulting P-P interval (PPI) and R-R interval (RRI) variation upon detection of an isolated VES. FIGS. 3(a) and (b) respectively show the atrial and ventricular event markers (in which VES is labeled by the arrow) and the resulting PPI and RRI variation without heart rate smoothing. Despite relatively stable atrial rhythm, a very short ventricular coupling interval due to VES is followed by a relatively long compensatory pause, generating the so-called short-long sequence. FIGS. 3(c) and (d) respectively show the resulting event markers and corresponding intervals if heart rate smoothing is activated. Immediately after VES detection, both chambers are captured by AV synchronous stimulation sequences, whose intervals are gradually prolonged until they reach the predefined basic interval (BI, 1000 ms in this example), or until sensed intrinsic event occurs, as indicated by the crossing point with the dotted line representing the estimated intrinsic interval.

Figure 4:
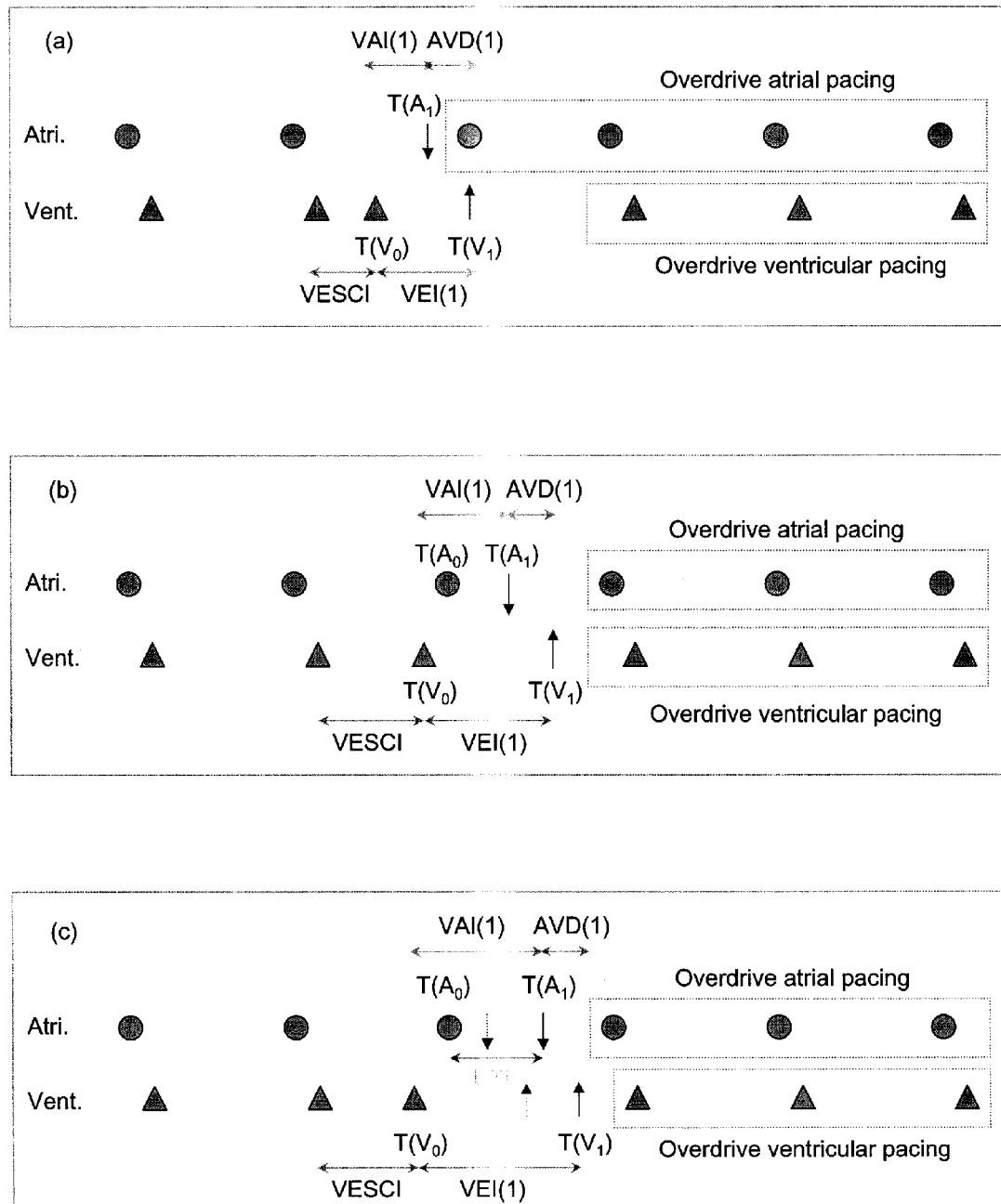
FIG. 4 illustrates the method for determining the first ventricular escape interval and the first VA interval upon detection of an isolated VES.

FIG. 4 illustrates the method for calculating VEI for the first ventricular stimulation pulse, VEI(1), and VAI for the first atrial stimulation pulse, VAI(1), upon detection of an isolated VES. Three different cases are illustrated.

In FIG. 4(a), the VES is detected at time $T(V_0)$ with ventricular coupling interval (VESCI). The greater value of VESCI and UTI is used to initially calculate VEI(1), by prolonging a fixed percentage or a fixed interval, while being limited by the predefined BI. The VAI(1) is then initially determined by subtracting an AV delay, AVD(1), from VEI (1). The AVD(1) can be a predefined fixed value, or preferably can be calculated dynamically based on VEI(1). The first atrial stimulation pulse will be delivered at time $T(A_1)$, the expiration time of VAI(1), if there is no sensed atrial event (atrial sense event) between $T(V_0)$ and $T(A_1)$. The first ventricular stimulation pulse will be delivered at time $T(V_1)$, the expiration time of VEI(1), if there is no sensed ventricular event (ventricular sense event) between $T(V_0)$ and $T(V_1)$. Otherwise, the heart rate smoothing algorithm is deactivated by the ventricular sense event.

In FIG. 4(b), VEI(1) and VAI(1) are similarly calculated as in case (a), but there is a sensed atrial event (atrial sense event) occurring at time $T(A_0)$, which is after VES detection and before the initially scheduled atrial stimulation pulse. The interval between $T(A_0)$ and $T(A_1)$ is then evaluated. If this interval is not shorter than the upper tracking interval UTI, then the initially calculated VEI(1) and VAI(1) remain the same. Any further atrial sense event between $T(A_0)$ and $T(A_1)$ or ventricular sense event between $T(V_0)$ and $T(V_1)$ will deactivate heart rate smoothing. Otherwise, the first pair of atrial and ventricular stimulation pulses will be delivered at $T(A_1)$ and $T(V_1)$, respectively.

Similar to case (b), FIG. 4(c) illustrates an example in which an intrinsic atrial event (atrial sense event) is sensed between $T(V_0)$ and the initially scheduled $T(A_1)$, as being marked by the dotted down arrow. However, in this case the interval between $T(A_0)$ and the initially scheduled $T(A_1)$ is shorter than UTI. To avoid potential competitive atrial pacing, $T(A_1)$ is postponed so that the resulting PPI equals to UTI. Correspondingly, the initially scheduled $T(V_1)$, as being marked by the dotted up arrow, is also rescheduled with proper AVD(1) after the updated $T(A_1)$. Similar to case (b), any atrial sense event between $T(A_0)$ and $T(A_1)$ or ventricular sense event between $T(V_0)$ and $T(V_1)$ will deactivate heart rate smoothing. Otherwise, the first pair of atrial and ventricular pacing pulses will be delivered at updated $T(A_1)$ and $T(V_1)$, respectively.

Figure 5:
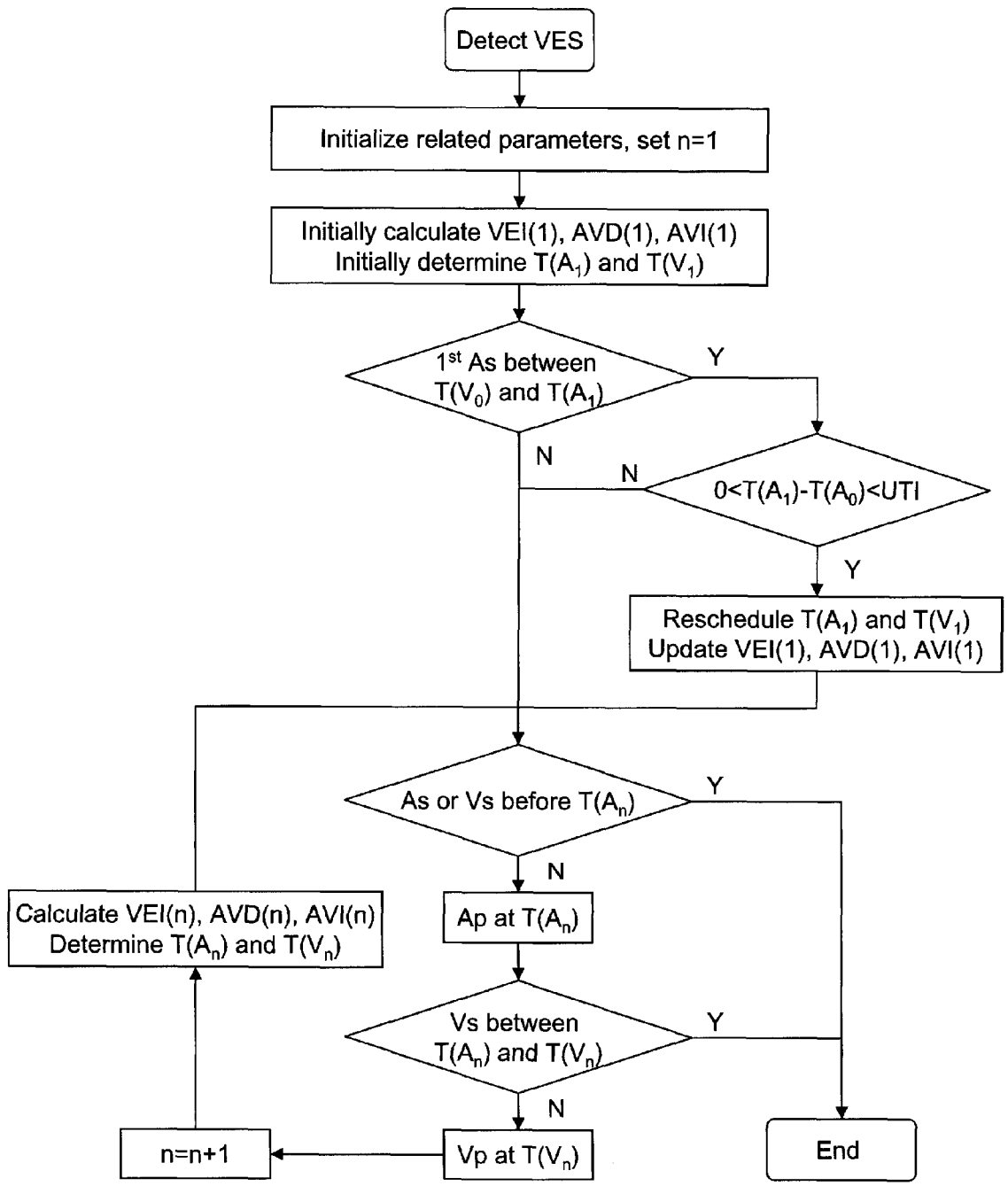
FIG. 5 shows a generalized flow chart of the present heart rate smoothing algorithm.

FIG. 5 shows a generalized flow chart of the present heart rate smoothing algorithm. Upon detection of a VES, the algorithm collects all necessary predefined parameters, and prepares to overdrive both atrium and ventricle by the first pair of AV synchronous pacing.

First, VEI(1) is calculated according to the following formula:

$$VEI(1) = \min(BI, \max(VESCI, UTI) \times (1+p)) \quad (1)$$

where p is a positive percentile value, preferably between 10% and 20%. Both UTI and BI are predefined values, preferably equal to 500 ms and 1200 ms, respectively. Alternatively, VEI(1) can also be calculated as:

$$VEI(1) = \min(BI, \max(VESCI, UTI) + \delta) \quad (2)$$

where δ is a fixed time increment, preferably between 50 ms and 100 ms. The time of the first ventricular stimulation pulse and the time of the first atrial stimulation pulse are respectively scheduled at:

$$T(V_1) = T(V_0) + VEI(1) \quad (3)$$

$$T(A_1) = T(V_1) - AVD(1) \quad (4)$$

Thus the first VAI after VES is determined as:

$$VAI(1) = T(A_1) - T(V_0) \quad (5)$$

Preferably, the following linear equation is used to obtain the n-th dynamic AVD corresponding to the n-th VEI:

$$AVD(n) = AV_{UTI} + k[VEI(n) - UTI] \quad (6)$$

where $$k = (AV_{BI} - AV_{UTI})/(BI - UTI) \quad (7)$$

Here, $AV_{BI}$ and $AV_{UTI}$ represent the predefined AVD at BI and UTI, respectively, thus the parameter k is a fixed constant once $AV_{BI}$ and $AV_{UTI}$ are programmed.

It is also noted that according to (6), AV delay (AVD) is dynamically adjusted based on current pacing interval (VEI). Therefore during post-VES heart rate smoothing, the actual AVD is very short (even if basic AVD is fixed and programmed long) because the ventricle is transiently paced at higher rate after VES. Such dynamic and short AVD will reduce the probability of monomorphic ventricular tachycardia beats falling into ventricular blanking periods (alternating between postatrial and postventricular blanking periods), thus minimizing the risk of ventricular undersensing and preventing potential interference with ventricular tachycardia detection (Viskin, 2001; Glikson et al., 2002).

If an atrial sense event is sensed at time $T(A_0)$, which is the first atrial sense event (if there are multiple) after the VES detection and before the initially scheduled atrial stimulation pulse, then the time interval between $T(A_0)$ and $T(A_1)$ is evaluated. If this interval is shorter than UTI, then $T(A_1)$ is rescheduled as following to prevent competitive atrial pacing:

$$T(A_1) = T(A_0) + UTI \quad (8)$$

Accordingly, both $T(V_1)$ and VEI(1) need to be updated:

$$T(V) = T(A_1) + AVD(1) \quad (9)$$

$$VEI(1) = T(V_1) - T(V_0) = VAI(1) + AVD(1) \quad (10)$$

Here, AVD(1) should be recalculated according to updated VEI(1). Substitute (10) into (6), it can be shown that:

$$AVD(1) = [AV_{UTI} + k(VAI(1) - UTI)]/(1-k) \quad (11)$$

If there is another atrial sense event between $T(A_0)$ and $T(A_1)$, or if there is a ventricular sense event between $T(V_0)$ and $T(V_1)$, then heart rate smoothing is deactivated. Otherwise, an atrial stimulation pulse is delivered at $T(A_1)$ when VAI(1) expires, and a ventricular stimulation pulse is delivered at $T(V_1)$ when VEI(1) expires. By this stage, both atrium and ventricle are captured, and the algorithm prepares the next pair of AV synchronous stimulation pulses. For the following pacing cycles, gradually prolonged VEI(n) with upper limit of BI, is calculated by:

$$VEI(n) = \min(BI, VEI(n-1) \times (1+p)) \quad (12)$$

or alternatively, $$VEI(n)=\min(BI, VEI(n-1)+\delta) \quad (13)$$

By backward shifting AVD(n) according to (6), the corresponding VAI(n) is obtained:

$$VAI(n)=VEI(n)-AVED(n) \quad (14)$$

Therefore, subsequent atrial stimulation pulses and ventricular stimulation pulses are scheduled according to determined VAI(n) and VEI(n), until heart rate smoothing is deactivated when an (intrinsic) atrial or ventricular sense event is sensed.

Figure 6:
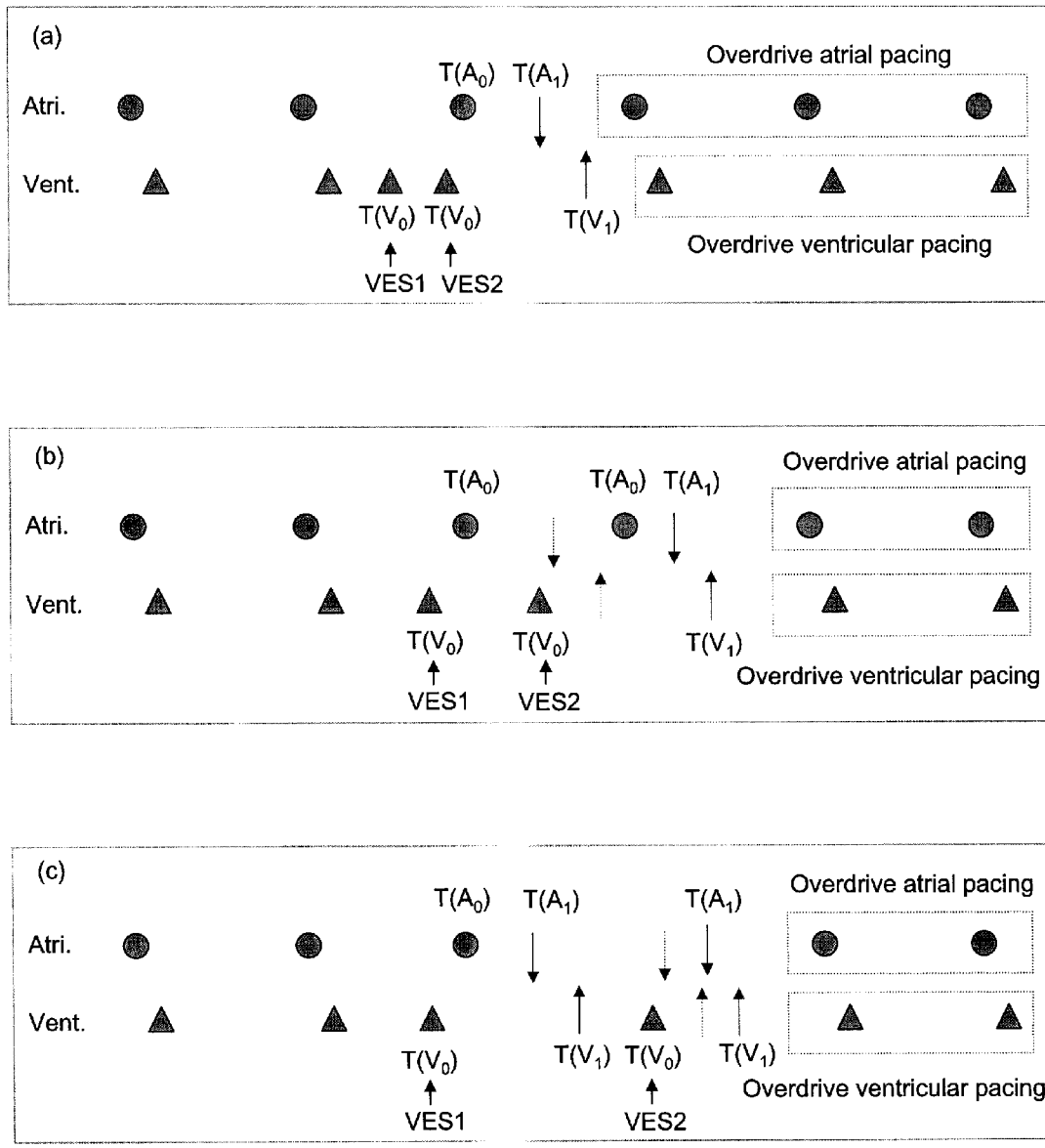
FIG. 6 illustrates three examples on automatic deactivation and proper reactivation of the heart rate smoothing algorithm in some special cases.

FIG. 6 illustrates three examples on automatic deactivation and proper reactivation of heart rate smoothing in some special cases.

FIG. 6(a) shows an example in which two closely coupled VESs are sensed before an atrial sense event. This could be a result of ventricular tachycardia, or may be due to false ventricular detection. Upon detection of the first VES (VES1), heart rate smoothing is activated. But before the expiration of its initially calculated VAI(1), the second VES (VES2) is sensed, whose effects are twofold: First, it deactivates the running heart rate smoothing algorithm. Second, it immediately reactivates another run of the heart rate smoothing algorithm. In other words, VES2 resets the heart rate smoothing algorithm. The pacing time $T(A_1)$ and $T(V_1)$ will be determined with respect to updated $T(V_0)$ which is set by VES2. Note despite the very short VESCI between VES1 and VES2, the resulting VEI(1) will not be shorter than UTI according to equation (1) or (2). A more general case of this example would include multiple closed coupled VESs (VES1, VES2, VES3, etc.) before an atrial sense event. Similarly, the heart rate smoothing algorithm will respond with an "activation-deactivation-reactivation-deactivation-... -reactivation" pattern. The first pair of atrial and ventricular stimulation pulses will be repetitively scheduled but not actually performed until there is a relatively long ventricular pause after the last VES. On the other hand, in the case of sustained ventricular tachycardia without such a long ventricular interval, no stimulation pulse will be delivered because any activation of the heart rate smoothing algorithm is immediately followed by deactivation, due to closely coupled ventricular sense event or atrial sense event before the expiration of VEI(1) (≥UTI). Therefore the present heart rate smoothing algorithm will not interfere with the ventricular tachycardia detection.

FIG. 6(b) shows an example of two consecutive VESs, or the so-called doublets. Heart rate smoothing is activated by the first VES (VES1), and initially schedules a point of time for an atrial stimulation pulse (marked by dotted down arrow) and ventricular stimulation pulse (marked by dotted up arrow). If the scheduled ventricular stimulation pulse is earlier than VES2, then both atrium and ventricle will be captured by overdrive pacing, thus VES2 will actually unlikely to happen. On the other hand, if VES2 is sensed earlier than the initially scheduled atrial stimulation pulse, than it resets the heart rate smoothing algorithm by a similar deactivation-reactivation sequence, and $T(A_1)$ and $T(V_1)$ will be determined with respect to updated $T(V_0)$ which is set by VES2. Another possibility is that VES2 is sensed between initially scheduled atrial and ventricular stimulation pulses (i.e., between the dotted arrows). In that case, the atrial stimulation pulse is delivered as initially scheduled, while the ventricular stimulation pulse is cancelled due to VES2-triggered deactivation. Thus the first atrial stimulation pulse and the sensed VES2 act synchronously without competitive ventricular pacing. Whether VES2 reactivates heart rate smoothing or not depends on whether VES2 is "recognized" as VES or not, by comparing the measured interval between atrial stimulation pulse and VES2 and the predefined VES coupling range limit. More generally, similar performance of the heart rate smoothing algorithm is expected in the presence of triplets or multiple consecutive VESs.

FIG. 6(c) illustrates another example in which overdrive pacing is intercepted by another VES. The heart rate smoothing algorithm is activated by the first VES (VES1) and delivers first pair of atrial and ventricular stimulation pulses at $T(A_1)$ and $T(V_1)$, respectively. But before the scheduled second pair of AV synchronous stimulation pulses (marked by the dotted down and up arrows), another VES (VES2) is sensed which resets heart rate smoothing by a similar deactivation-reactivation sequence. If VES2 occurs between the scheduled atrial stimulation pulse and ventricular stimulation pulse, the scheduled atrial stimulation pulse will be delivered while the ventricular stimulation pulse will be cancelled similar to the case as being discussed in FIG. 4(b). More generally, any VES being sensed during the course of heart rate smoothing will reset the heart rate smoothing algorithm. The success deactivation without immediate reactivation of the algorithm occurs when an intrinsic atrial event is sensed, or an atrial stimulation pulse is followed by a ventricular sense event with reasonable AV delay (i.e., not detected as VES).

The invention claimed is:

1. An implantable cardiac electrostimulator comprising:
   an atrial sensing channel for processing intracardiac electrogram signals and for detecting signals corresponding to atrial activity and for generating an atrial sense event signal upon detection of a signal corresponding to atrial activity,
   a ventricular sensing channel for processing intracardiac electrogram signals and for detecting signals corresponding to ventricular activity and for generating a ventricular sense event signal upon detection of a signal corresponding to ventricular activity,
   a ventricular extrasystole (VES) detector being operatively connected to said atrial and ventricular sensing channels and being adapted to detect ventricular extrasystoles,
   an atrial stimulation pulse generator,
   a ventricular stimulation pulse generator,
   a stimulation control unit being operatively connected to said atrial stimulation pulse generator and said ventricular stimulation pulse generator, said stimulation control unit being adapted to:
   (1) determine a scheduled time of delivery of an atrial stimulation pulse (T(A)) and a scheduled time of delivery of ventricular stimulation pulse (T(V)),
   (2) trigger said atrial stimulation pulse generator or said ventricular stimulation pulse generator at the scheduled point of time T(A) or T(V), respectively, if no atrial sense event signal is generated before time out of an atrial escape interval (VAI), said atrial escape interval timing out at T(A), or if no ventricular sense event signal is generated before time out of a ventricular escape interval (VEI), said ventricular escape interval timing out at T(V), respectively,
   (3) modify T(A) and T(V) upon detection of a ventricular extra systole while maintaining a proper atrioventricular synchrony by setting a physiologically adequate A-V delay between T(A) and corresponding T(V), and
   (4) respond to detection of the ventricular extra systole by setting a shortened interval between the ventricular extra systole and a subsequent T(A), and between the ventricular extra systole and a subsequent T(V), to a shorter interval of time than a base interval (BI), wherein the base interval BI at least approximates the interval between two consecutive T(A), and/or between two consecutive T(V), in the absence of a ventricular extra systole.

2. The electrostimulator according to claim 1, wherein said stimulation control unit is adapted to gradually extend said shortened interval between subsequent consecutive T(A), and subsequent consecutive T(V), from heart cycle to heart cycle until the interval corresponds to the base interval (BI), or until a sense event signal is generated.

3. The electrostimulator according to claim 1, wherein said stimulation control unit is adapted to set the base interval to an intrinsic interval sensed in absence of a ventricular extra systole by determining the time period between two consecutive ventricular sense events.

4. The electrostimulator according to claim 1, wherein said VES detector is adapted to generate a VES detection signal depending on evaluation of the duration of a coupling interval between a ventricular sense event and the preceding atrial event.

5. The electrostimulator according to claim 1, wherein said VES detector is adapted to generate a VES detection signal depending on detection of a sudden decrease in duration of an interval between two consecutive ventricular events.

6. The electrostimulator according to claim 1, wherein said VES detector is adapted to generate a VES detection signal depending on a morphology analysis of a recorded intracardiac electrogram (IEGM).

7. The electrostimulator according to claim 1, wherein the electrostimulator is at least one of a dual chamber pacemaker, a cardioverter/defibrillator, or a multi-chamber pacemaker for cardiac resynchronization therapy.

8. An implantable cardiac electrostimulator comprising:
   an atrial sensing channel for processing intracardiac electrogram signals and for detecting signals corresponding to atrial activity and for generating an atrial sense event signal upon detection of a signal corresponding to atrial activity,
   a ventricular sensing channel for processing intracardiac electrogram signals and for detecting signals corresponding to ventricular activity and for generating a ventricular sense event signal upon detection of a signal corresponding to ventricular activity,
   a ventricular extrasystole (VES) detector being operatively connected to said atrial and ventricular sensing channels and being adapted to detect ventricular extrasystoles,
   an atrial stimulation pulse generator,
   a ventricular stimulation pulse generator,
   a stimulation control unit being operatively connected to said atrial stimulation pulse generator and said ventricular stimulation pulse generator, said stimulation control unit being adapted to:
   (1) determine a scheduled time of delivery of an atrial stimulation pulse (T(A)) and a scheduled time of delivery of ventricular stimulation pulse (T(V)),
   (2) trigger said atrial stimulation pulse generator or said ventricular stimulation pulse generator at the scheduled point of time T(A) or T(V), respectively, if no atrial sense event signal is generated before time out of an atrial escape interval (VAI), said atrial escape interval timing out at T(A), or if no ventricular sense event signal is generated before time out of a ventricular escape interval (VEI), said ventricular escape interval timing out at T(V), respectively,
   (3) modify T(A) and T(V) upon detection of a ventricular extra systole while maintaining a proper atrioventricular synchrony by setting a physiologically adequate A-V-delay between T(A) and corresponding T(V), and
   (4) perform a synchronous heart rate smoothing algorithm, said algorithm comprising calculating a first ventricular escape interval (VEI) beginning with a ventricular extra systole and ending with a scheduled ventricular stimulation pulse T(V) said calculation being based on a time duration between the ventricular extra systole and the preceding ventricular event, said calculated ventricular escape interval being longer than said duration between the ventricular extra systole and the preceding ventricular event and being shorter than a base interval (BI) being applicable in the absence of a ventricular extra systole.

9. The electrostimulator according to claim 8, wherein said stimulation control unit is adapted to determine an A-V-delay (AVD) being the time interval between a scheduled ventricular stimulation pulse T(V) and the preceding atrial event based on said calculated ventricular escape interval (VEI).

10. The electrostimulator according to claim 9, wherein said stimulation control unit is adapted to determine a scheduled point of time T(A) of triggering an atrial stimulation pulse based on said first ventricular escape interval and said A-V-delay, thus defining a first V-A-interval.

11. The electrostimulator according to claim 10, wherein said stimulation control unit is adapted to reschedule said point of time T(A) of triggering an atrial stimulation pulse when necessary to prevent competitive atrial pacing.

12. The electrostimulator according to claim 11, wherein said stimulation control unit is adapted to reschedule said point of time T(A) of triggering an atrial stimulation pulse:
   a. by evaluating the time interval between the first atrial sense event after VES and the originally scheduled point of time T(A) of delivery of the first atrial stimulation pulse, and also
   b. by ensuring that a resulting interval between the first atrial sense event after VES and the originally scheduled point of time T(A) is greater than or equal to a predefined minimum interval.

13. The electrostimulator according to claim 12, wherein said predefined minimum interval is a predefined upper tracking interval (UTI).

14. The electrostimulator according to claim 12, wherein said stimulation control unit is adapted to update said first ventricular escape interval when said point of time T(A) of triggering an atrial stimulation pulse is rescheduled.

15. The electrostimulator according to claim 10, wherein said stimulation control unit is adapted to exit said synchronous heart rate smoothing algorithm upon occurrence of an atrial sense event before expiration of said VA interval, or a ventricular sense event before expiration of said ventricular escape interval (VEI).

16. An implantable cardiac electrostimulator including:
   a. an atrial sensing channel configured to generate an atrial sense event signal in response to an intrinsic atrial event;
   b. a ventricular sensing channel configured to generate a ventricular sense event signal in response to an intrinsic ventricular event;
   c. a ventricular extrasystole (VES) detector operatively connected to the atrial and ventricular sensing channel and configured to detect a ventricular extrasystole;
   d. an atrial stimulation pulse generator;
   e. a ventricular stimulation pulse generator;
   f. a stimulation control unit operatively connected to the atrial stimulation pulse generator and the ventricular stimulation pulse generator, the stimulation control unit being configured to:
   (1) trigger the atrial stimulation pulse generator at a scheduled atrial stimulation pulse delivery time T(A) if no atrial sense event signal is generated before time out of an atrial escape interval (VAI), the atrial escape interval VAI timing out at T(A), (2) trigger the ventricular stimulation pulse generator at a scheduled ventricular stimulation pulse delivery time T(V) if no ventricular sense event signal is generated before time out of a ventricular escape interval (VEI), the ventricular escape interval VEI timing out at T(V), (3) set an AV delay between T(A) and a subsequent T(V), thereby maintaining atrioventricular synchrony, (4) modify T(A) and T(V) in dependence on detection of any ventricular extrasystole (VES), and (5) determine a first ventricular escape interval (VEI) beginning with a ventricular extrasystole (VES) and ending with a scheduled ventricular stimulation pulse T(V), the first ventricular escape interval (VEI) being:
  i. longer than the duration of the interval between the ventricular extrasystole (VES) and the preceding intrinsic ventricular event, and
  ii. shorter than a base interval (BI), the base interval (BI) being at least substantially equal to an interval between two consecutive intrinsic ventricular events in the absence of a ventricular extrasystole (VES).

17. The electrostimulator of claim 16 wherein the VES detector is configured to detect a ventricular extrasystole (VES) in dependence on the duration of an interval between an atrial sense event and a subsequent ventricular sense event.

18. The electrostimulator of claim 16 wherein the VES detector is configured to detect a ventricular extrasystole (VES) in dependence on the duration of an interval between consecutive ventricular sense events.

19. The electrostimulator of claim 16 wherein the VES detector is configured to detect a ventricular extrasystole (VES) from an intracardiac electrogram (IEGM).

20. The electrostimulator of claim 16 wherein the stimulation control unit is configured to determine an A-V delay (AVD) between a scheduled ventricular stimulation pulse delivery time T(V) and the preceding intrinsic atrial event based on the first ventricular escape interval (VEI).

21. The electrostimulator of claim 20 wherein the stimulation control unit is configured to determine a scheduled atrial stimulation pulse delivery time T(A) based on the first ventricular escape interval (VEI) and the A-V delay (AVD), thus defining a first V-A interval (VAI).

22. The electrostimulator of claim 21 wherein the stimulation control unit is configured to reschedule the scheduled atrial stimulation pulse delivery time T(A) if the time interval between the scheduled atrial stimulation pulse delivery time T(A) and a prior time T(Ao) of an intrinsic atrial event is less than an upper tracking interval (UTI).

23. The electrostimulator of claim 21 wherein the stimulation control unit is configured to reschedule the scheduled atrial stimulation pulse delivery time T(A) if the time interval between:
  a. the first atrial sense event after a ventricular extrasystole (VES), and
  b. the scheduled atrial stimulation pulse delivery time T(A),
is shorter than a predefined minimum interval.

24. The electrostimulator of claim 23 wherein the predefined minimum interval is a predefined upper tracking interval (UTI).

25. The electrostimulator of claim 23 wherein the stimulation control unit is configured to update the first ventricular escape interval (VEI) when the scheduled atrial stimulation pulse delivery time T(A) is rescheduled.

26. The electrostimulator of claim 21 wherein the stimulation control unit is configured to cancel delivery of the scheduled ventricular stimulation pulse T(V) upon occurrence of:
  a. an atrial sense event before expiration of the V-A interval (VAI), or
  b. a ventricular sense event before expiration of the ventricular escape interval (VEI).

27. An implantable cardiac electrostimulator including:
  a. an atrial sensing channel configured to generate an atrial sense event signal in response to an intrinsic atrial event;
  b. a ventricular sensing channel configured to generate a ventricular sense event signal in response to an intrinsic ventricular event;
  c. a ventricular extrasystole (VES) detector operatively connected to the atrial and ventricular sensing channel and configured to detect a ventricular extrasystole;
  d. an atrial stimulation pulse generator;
  e. a ventricular stimulation pulse generator;
  f. a stimulation control unit operatively connected to the atrial stimulation pulse generator and the ventricular stimulation pulse generator, the stimulation control unit being configured to:
    (1) trigger the atrial stimulation pulse generator at a scheduled atrial stimulation pulse delivery time T(A) if no atrial sense event signal is generated before time out of an atrial escape interval (VAI), the atrial escape interval VAI timing out at T(A),
    (2) trigger the ventricular stimulation pulse generator at a scheduled ventricular stimulation pulse delivery time T(V) if no ventricular sense event signal is generated before time out of a ventricular escape interval (VEI), the ventricular escape interval VEI timing out at T(V),
    (3) set an AV delay between T(A) and a subsequent T(V), thereby maintaining atrioventricular synchrony,
    (4) modify T(A) and T(V) in dependence on detection of any ventricular extrasystole (VES), and
    (5) respond to detection of a ventricular extrasystole (VES) by setting at least one of:
      i. an interval between the ventricular extrasystole (VES) and a subsequent T(V), the interval being shorter than a base interval (BI), the base interval (BI) being at least substantially equal to an interval between two consecutive intrinsic ventricular events in the absence of a ventricular extrasystole (VES), and
      ii. an interval between the ventricular extrasystole (VES) and a subsequent T(A), the interval being shorter than a base interval (BI), the base interval (BI) being at least substantially equal to an interval between two consecutive intrinsic atrial events in the absence of a ventricular extrasystole (VES).

28. The electrostimulator of claim 27 wherein the stimulation control unit is configured to subsequently gradually extend at least one of:
  a. the interval between two consecutive T(V), and
  b. the interval between two consecutive T(A), from heart cycle to heart cycle until:
    (1) the interval corresponds to the base interval (BI), or
    (2) an intrinsic ventricular event occurs.

29. The electrostimulator of claim 27 wherein the stimulation control unit is configured to set the base interval (BI) by determining the interval between two consecutive ventricular sense events in the absence of a ventricular extrasystole (VES).

* * * * *